US005914660A

United States Patent [19]

Mesibov et al.

[11] Patent Number: 5,914,660
[45] Date of Patent: Jun. 22, 1999

[54] POSITION MONITOR AND ALARM APPARATUS FOR REDUCING THE POSSIBILITY OF SUDDEN INFANT DEATH SYNDROME (SIDS)

[75] Inventors: Barbara Mesibov, Mill Neck, N.Y.; Leonard R. Clark, Jr., Oreland, Pa.

[73] Assignee: Waterview LLC, East Norwich, N.Y.

[21] Appl. No.: 09/047,357

[22] Filed: Mar. 26, 1998

[51] Int. Cl.[6] .................................................. G08B 23/00
[52] U.S. Cl. .................. 340/573; 340/573.1; 340/573.4; 340/575; 340/517
[58] Field of Search ............................... 340/573.1, 575, 340/517, 689, 524, 521, 573.4, 573.7

[56] References Cited

U.S. PATENT DOCUMENTS

| | | | |
|---|---|---|---|
| 3,831,586 | 8/1974 | Petit | 340/573 |
| 4,196,425 | 4/1980 | Williams et al. | 340/573 |
| 4,279,257 | 7/1981 | Hochstein | 340/573 |
| 4,696,307 | 9/1987 | Montgieux | 340/573 |
| 4,972,177 | 11/1990 | Nolan | 340/573 |
| 5,081,447 | 1/1992 | Echols | 340/573 |
| 5,153,584 | 10/1992 | Engira | 340/870.18 |
| 5,299,332 | 4/1994 | Perng | 340/573 |
| 5,400,012 | 3/1995 | Walton | 340/573 |
| 5,471,198 | 11/1995 | Newham | 340/573 |
| 5,534,851 | 7/1996 | Russek | 340/573 |
| 5,684,460 | 11/1997 | Scanlon | 340/573 |
| 5,686,882 | 11/1997 | Giani | 340/573 |
| 5,774,055 | 6/1998 | Pomerantz | 340/573 |
| 5,796,340 | 8/1998 | Miller | 340/573 |

OTHER PUBLICATIONS

Tucker, Miriam E. "Drop in SIDS Attributed to 'Back to Sleep' Campaign", *Pediatric News*, Dec. 1997.

*Primary Examiner*—Jeffery A. Hofsass
*Assistant Examiner*—Anh La
*Attorney, Agent, or Firm*—Michael de Angeli

[57] ABSTRACT

A device for reducing the possibility of sudden infant death syndrome (SIDS) comprises a position-indicating device effectively coupled to a signal-producing circuit and attached to the clothing of the infant. The position-indicating device provides signals varying in response to prone and other positions assumed by the infant during sleep, allowing an associated alarm device to be activated in response to the infant's assuming a SIDS-dangerous prone or side-lying position. In one embodiment, the position of the infant can be determined by an optical sensor interacting with a reflective or other marker adhered to the infant. Gravity or pressure switches may also be used to provide position-responsive signals. A signal generated upon assumption of the SIDS-dangerous prone or side-lying positions is transmitted to a remote receiver located proximate the infant's care-giver whereupon an alarm is generated to indicate the need to reposition the infant. A constant low-level or intermittent maintenance signal can be produced to assure the continued and proper operation of the apparatus. An additional awakening alarm can be produced near the sleeping infant to further reduce the likelihood of a SIDS event.

17 Claims, 2 Drawing Sheets

POSITION MONITOR AND ALARM APPARATUS FOR REDUCING THE POSSIBILITY OF SUDDEN INFANT DEATH SYNDROME (SIDS)

FIELD OF THE INVENTION

The present invention relates to an apparatus for continuously monitoring the position assumed by a sleeping infant. More particularly, the invention relates to the provision of an alarm to indicate when the infant has taken a position considered to be conducive to the onset of Sudden Infant Death Syndrome (SIDS).

BACKGROUND OF THE INVENTION

Sudden Infant Death Syndrome (SIDS) has been defined as the "sudden death of an infant under one year of age which remains unexplained after a thorough case investigation, including performance of a complete autopsy, examination of the death scene, and a review of the clinical history." SIDS occurs in all types of families and is generally independent of race and socioeconomic level. It is unexpected and usually occurs in apparently healthy infants from one month to one year of age. Death occurs without warning and is accompanied by no signs of suffering. Five to six thousand infant deaths per year were attributed to SIDS during the late eighties and early nineties.

The horror of SIDS, also commonly known as "crib death", lies in the thus far unsolved mystery of why a seemingly healthy baby dies suddenly, without warning and without apparent reason. A form of undiagnosed apnea has been suspected; various maternal risk factors, including cigarette smoking during pregnancy, maternal age less than 20 years, poor prenatal care, low weight gain, anemia, drug abuse and a history of sexually transmitted disease and/or urinary tract infection have all been suspected of heightening the likelihood of occurrence; and the presence of soft bedding materials and the breathing of second-hand smoke have also been cited as possible contributing factors. Recent studies at the National Institute of Child Health and Human Development (NICHD) have identified defects in the regions of the brains of SIDS-susceptible infants that control breathing. However, whatever the root cause of SIDS is eventually determined to be, it appears that pro-active parenting can substantially reduce the risk to the newborn.

More specifically, in 1992 the American Academy of Pediatrics recommended that babies be placed on their backs or sides to sleep, and subsequently modified this to recommend that babies be placed only on their backs to sleep. This recommendation was based on a number of studies conducted in Australia, New Zealand, Wales and elsewhere and was subsequently embraced by the NICHD as the cornerstone of a campaign called "Back to Sleep" launched in 1994. It is estimated that more than fifty percent of all SIDS deaths can be prevented if babies are prevented from maintaining a prone, face-down position during sleep; as mentioned, it also appears desirable to avoid the side-lying position.

Two approaches have been suggested to prevent SIDS or crib death. First, the infant can be denied the freedom to position itself in the dangerous face-down position—but this requires cumbersome and restrictive bedding, clothing or harnessing arrangements that introduce inconvenience, discomfort and perhaps a new set of hazards. The second approach involves monitoring the breathing of the infant so that a cessation of breathing can be timely recognized and intervention effected.

Two devices in the prior art suggest monitoring the breathing of an infant as a method of preventing SIDS, but differ in implementation. The device in U.S. Pat. No. 4,696,307 comprises a detection and signaling device attached to the body of the infant and responsive to the body displacements produced on the skin of the infant as it breathes. The breathing monitor of U.S. Pat. No. 5,400,012 proposes a fluid-filled bladder elastically attached to the infant to provide flexible and sensitive coupling between the infant and a breathing monitor including an LED and an alarm to report breathing and cessation of breathing respectively. The utility of both of these breathing monitors are limited by difficult attachment and delicate sensitivity issues presented when designing such sophisticated instrumentation for monitoring a tiny infant. Neither seems to have found a commercially viable niche.

OBJECTS OF THE INVENTION

It is therefore an object of the present invention to reduce the likelihood of Sudden Infant Death Syndrome (SIDS) resulting from the cessation of breathing of an infant resulting from cardiorespiratory failure, or other undetermined causes, associated with the prone, that is, face-down, or side-lying sleeping positions, by continuously monitoring the position assumed by the infant in a crib, and in particular to actuate an alarm when the infant moves away from the face-up position.

It is another object of the invention to provide an apparatus to sense the position taken by a sleeping infant and to provide an alarm signal to a care-giver whereby the care-giver can adjust the position as needed to minimize the likelihood of SIDS.

It is a further object of the invention to provide a reliable and inexpensive system to monitor the position of a sleeping infant.

It is a further object of the invention to provide remote care-givers with sufficient warning of potentially dangerous conditions to provide time to adjust the position assumed by a sleeping infant and thereby minimize the likelihood of SIDS.

It is a further object of the invention to provide a multiplexed alarm device for disposition at a nurses' station in a hospital nursery or the like for providing an alarm signal if any of a number of associated monitors indicate that a corresponding infant is in a SIDS-susceptible position.

SUMMARY OF THE INVENTION

According to one embodiment of the invention, the position of the infant can be determined by a remote sensor interacting with a marker secured to the infant or its clothing. In a preferred embodiment, an infrared source and sensor pair are provided; the infant wears clothing having varying infrared reflectivity, so that the sensor detects differing amounts of infrared reflection depending on the infant's position. A signal generated upon the infant's assumption of the SIDS-dangerous prone position is transmitted to a remote receiver located proximate the infant's care-giver whereupon an alarm is generated to indicate the need to reposition the infant. Alternatively a position-sensing transducer is affixed to the body or clothing of the infant. The transducer is calibrated to distinguish between prone and other positions assumed by the infant during sleep, and transmits a signal to a remote alarm device when appropriate.

A constant low-level or intermittent maintenance signal can be produced to assure the continued and proper operation of the apparatus. An additional awakening alarm can be produced near the sleeping infant to further reduce the likelihood of a SIDS event.

BRIEF DESCRIPTION OF THE DRAWINGS

The invention will be better understood if reference is made to the accompanying drawings, wherein.

DESCRIPTION OF THE PREFERRED EMBODIMENTS

Figure 1:
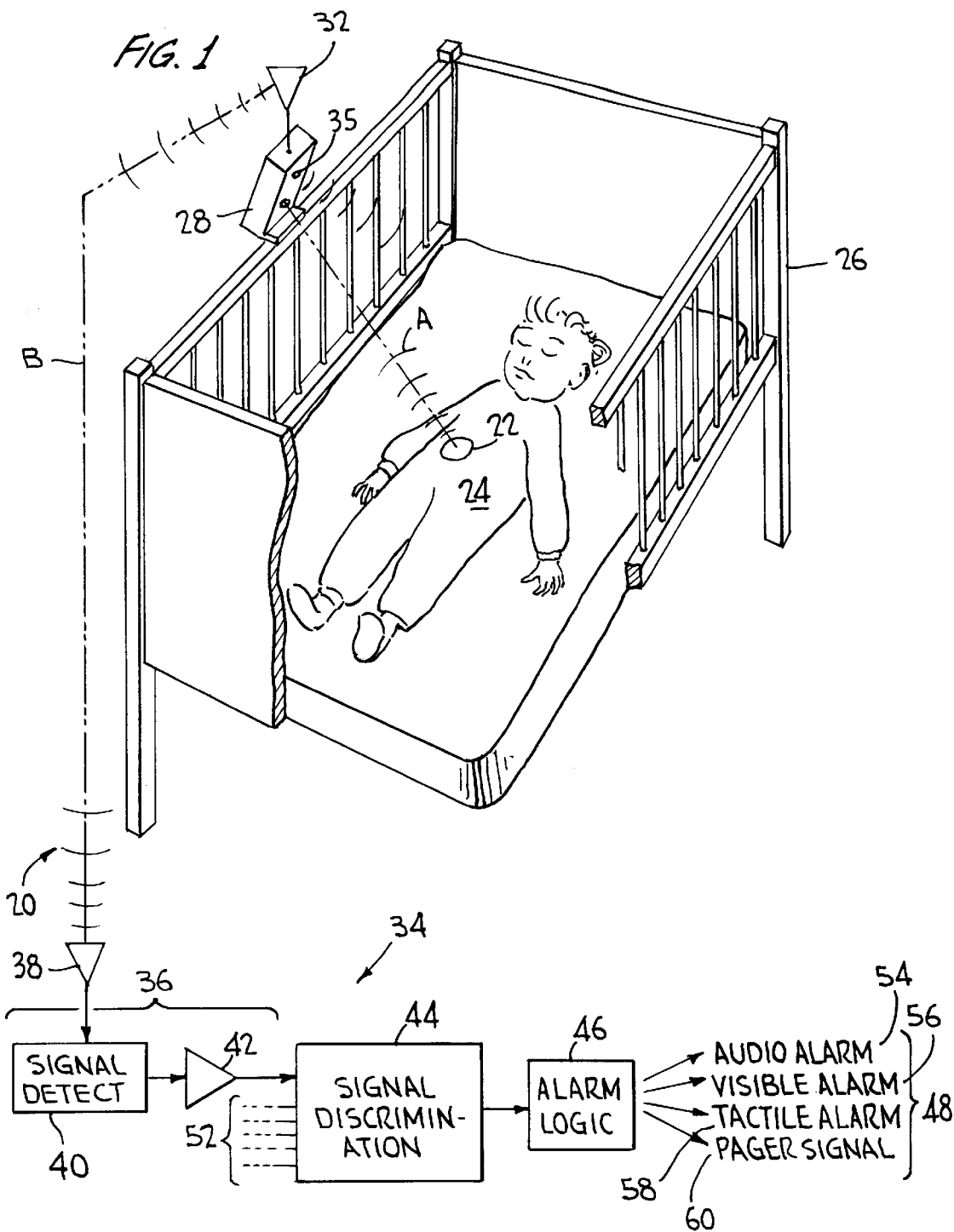
FIG. 1 shows schematically the arrangement of the components of the infant position monitor and alarm apparatus of the present invention in a first embodiment of the present invention.
Figure 2:
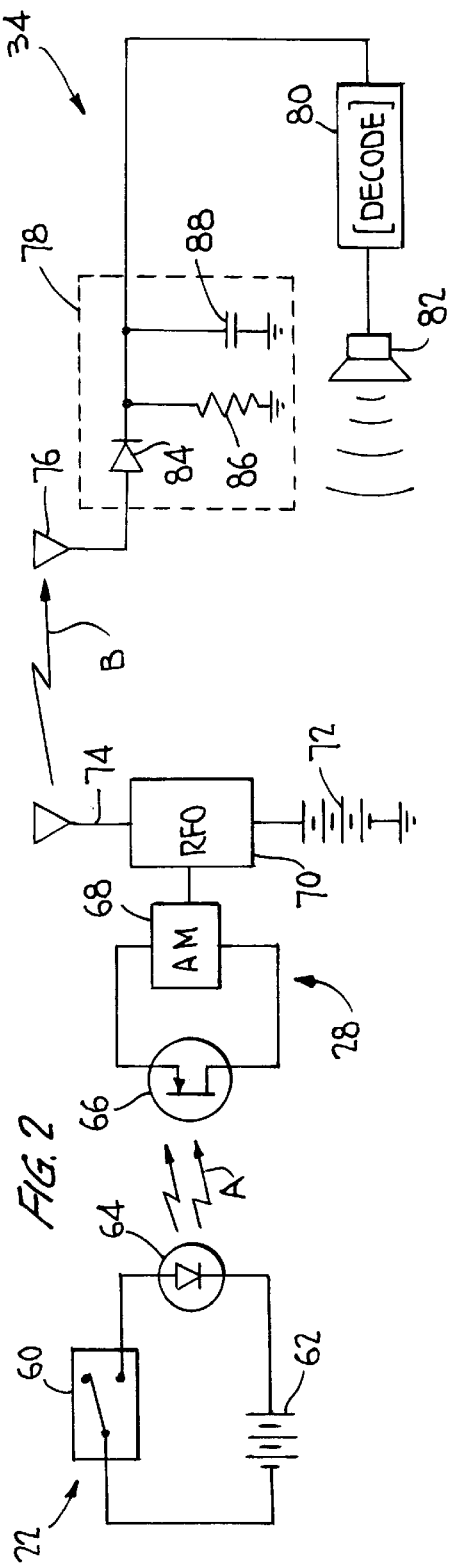
FIG. 2 is a simplified block diagram of the principal components of a first embodiment of the present invention.

Stated generally, and as shown in FIGS. 1 and 2, in a first embodiment the apparatus 20 of the present invention for monitoring the postion of a sleeping infant and thus reducing the likelihood of SIDS comprises a device 22 for detecting when an infant moves into a dangerous side-lying or prone position, a transceiver 28 to transmit a signal indicative of this condition, and a remotely located receiver 34 to actuate an alarm to alert a care-giver of the need to attend to and reposition the infant.

More particularly, in the embodiment shown in FIG. 1, the SIDS prevention monitor apparatus 20 of the present invention includes an assembly 22 of a position-sensing transducer and a device for transmitting a signal indicative of the position of the infant. This assembly is affixed to the diaper or other sleepwear 24 of an infant in a crib 26, and is arranged so that a change in the signal transmitted is indicative of a change in body position assumed by the infant, e.g., from a safe supine to a more dangerous side-lying or prone position.

As discussed in further detail below, numerous types of position transducers can be provided, and may be operated in several different but equivalent ways to provide a useful signal. For example, gravity switches, such as mercury switches, can be arranged so as to be closed if the infant assumes the SIDS-susceptible prone position; this switch closure can be employed to cause a radio-frequency or infrared signal to be sent to an associated alarm device. Of course, the inverse arrangement, wherein the switch is opened if the infant assumes the prone postion, is also possible. The latter embodiment will be particularly useful if a signal is transmitted at regular intervals, and detected by an associated transceiver to verify correct operation of the device; in this arrangement, interruption of transmission would be detected by the transceiver and employed to activate the alarm. The switch could also be arranged so as to be closed only when the infant is in the supine, i.e., face-up, postion, so as to be closed if the infant rolls into the side-lying or prone positions. In each of these cases the change of state of the transducer triggers the alarm.

Further alternatives include implementation of the transducer as a pressure switch, e.g., worn on the infant's chest, so as to be closed if the infant rolls into the prone position. An infrared or radio-frequency transmitter on the infant's chest could be arranged to send a signal every ten seconds, for example, to be detected by an associated transceiver; if the signal were not received at the appointed time, for example, if the line-of-sight between transmitter and transceiver were blocked by the infant's having rolled over, the alarm could be given.

These implementations of the principles of the invention would normally require the infant to wear a device including a battery, to power any of the types of transmission noted. Employment of a battery might render the device uncomfortably large or heavy, and would involve the risk of failure if the battery became discharged. Several types of marker device for allowing an associated device to sense the infant's position that do not require a battery are expressly contemplated, and these and equivalent others are within the scope of the invention. For example, a coil of wire having a known impedance could be provided, and opened (or closed) by a switch operated upon movement of the infant between safe and dangerous positions; the accompanying change in impedance can easily be noted by an associated powered device, which would then provide the alarm signal to a remote device for alerting the care-giver. Again, in each case the change of state of the transducer triggers the alarm.

A particularly preferred alternative discussed in detail below includes implementing the marker as an optical target, e.g., a reflective surface, on the infant's clothing, coupled with a video or optical sensor for measuring the amount of reflected light, determining the infant's position responsive thereto, and alerting a care-giver upon assumption of a SIDS-susceptible position.

Returning to discussion of the embodiment of FIG. 1, a transceiver 28 provided in a physical package suitable for being readily attached to or disposed near the crib is capable of sensing the position-indicating signal A produced by position-sensing apparatus 22, processing this signal, and transmitting a second signal B of sufficient transmission strength to be detected by a remote receiver located in the presence of the infant's care-giver. As will be apparent to those of skill in the art, transceiver 28 is implemented in a manner corresponding to the implementation of position-sensing apparatus 22. That is, transceiver 28 operates to provide a signal responsive to the infant's position, typically by detecting a change of state in the signal provided by position-sensing apparatus 22. Transceiver 28 may also comprise an optical or video device to detect any change of position of the infant, again as discussed in detail below.

The signal B transmitted by transceiver 28 is shown in FIG. 1 as a wireless signal, again typically an infrared or radio-frequency signal transmitted by an antenna 32, but it is also within the scope of the invention to connect the transceiver to an associated alarm device by a "hard-wired" connection. Such hard-wired connections include both wiring installed specifically for this purposes, and employment of preexisting wiring; as an example of the latter, the invention may be implemented using existing household wiring to carry the signals from transceiver 28, using the same componentry and techniques now commonly employed to transmit intercom signals over household wiring. This has the evident advantage of allowing an associated alarm device to be plugged anywhere within the household without installation of additional wiring.

Implementation of the invention employing a hard-wired connection between transceiver 28 and an associated alarm device is particularly desirable in relatively permanent installations, such as when a number of transceivers 28 are connected to a single central alarm device, for example, at a nurses' station in a hospital nursery or the like. Such a central alarm device might have, for example, a number of individual lamps or LEDs corresponding to the individual cribs, as well as an audible alarm. For example, if an alarm were received from a transceiver 28, an audible alarm might be given, alerting a nurse that an infant was in danger, while the corresponding lamp would also be lit, enabling the nurse to identify the infant in danger. Provision of wireless communication in these circumstances is also within the scope of the invention, of course, but measures (which are within the skill of the art) would be required to ensure correct correlation of the lamps with the transceivers.

In response to detection of the signal from transceiver 28, an associated alarm device 34 activates an alarm to alert the care-giver of the need to awaken and/or reposition the child in response to an indication that the infant has assumed a SIDS-dangerous sleeping position. Optionally, an additional infant alarm indicated at 35 located near the crib, e.g., comprised by transceiver 28, can be activated upon detection of a prone sleeping position to awaken the child.

As shown in FIG. 1, the principal components of associated alarm device 34 are a device 36 for detecting the signal transmitted by transceiver 28, signal discrimination circuitry 44, alarm logic circuitry 46, and one or more alarm devices 48. Again, numerous alternatives as to each, selected corresponding to the particular system attributes desired, are within the scope of the invention. For example, the device 36 for detecting the signal transmitted by transceiver 28 is shown as comprising an antenna 38, signal detection circuitry 40, and amplifier 42; a system implemented using radio-frequency communication might be thus implemented. Infrared communication would involve corresponding components, similarly within the skill of the art; a hard-wired connection, by comparison, would be very simple, albeit more complicated to install.

Similarly, the signal discrimination circuitry 44 would vary widely depending on the actual implementation involved. In a radio-frequency or infrared system intended for home use, the principal technical problem would be in avoiding "false alarms" caused by other household devices while providing reliable communication. In a hard-wired, multiple-transceiver embodiment (as indicated by a number of lines 52 extending to further transceivers, not shown) signal discrimination circuitry 44 would most probably perform time-division multiplexing, wherein the status of each transceiver is verified on the order of once per second, and communicated to alarm logic 46, e.g., for illuminating appropriate ones of pairs of green and red lamps accordingly.

As suggested, alarm logic 46 may respond to the signals provided by transceiver(s) in any of a number of ways, again depending on system implementation. Perhaps the simplest alarm is to provide an audio alarm, e.g., by bell or siren, as indicated at 54. This could be supplemented by a flashing light or other visible alarm, as suggested at 56, or perhaps a tactile alarm 58 (such as those given restaurant patrons). Pager technology as suggested at 60 could also be provided, i.e., a device functionally similar to a current pager could be activated responsive to a signal directly from transceiver 28 or from alarm device 34.

FIG. 2 shows the basic circuit components of each of the elements of one embodiment of the invention in highly schematic form. In this embodiment, position-sensing apparatus 22 may typically comprise a position-sensitive transducer 60, closed when the infant assumes the SIDS-susceptible prone position, a power source 62, such as a battery, and a transmitting element 64 to produce a first position-indicating signal A received by transceiver 28. In this case, transmitting element 64 is illustrated as an infrared-emitting LED.

Transceiver 28 comprises a device to detect the first signal from element 64, in this case an infrared-sensitive phototransistor 66. Transistor 66 activates an amplitude modulator 68, which in turn controls emission of a second radio-frequency signal B produced by radio-frequency oscillator 70, powered by power supply 72 and transmitted by antenna 74. Provision of modulation, e.g., encoding the transmission of the radio-frequency signal B according to a predetermined pattern, enables discrimination between signals provided by this unit and other household signal sources.

Finally, in this embodiment the associated alarm device 34 comprises an antenna 76 for detecting signal B transmitted by transceiver 28, a detection circuit 78, signal discrimination circuitry if deemed necessary 80, and an alarm device 82. Detection circuit is shown schematically as a simple AM detector comprising a diode 84, a resistor 86, and a capacitor 88; those of skill in the art will recognize that numerous more sophisticated but functionally equivalent detection circuits are available. If desired, a decoder can provide signal discrimination functions as necessary, so that alarm 82 is activated only after the detected signal has been examined and determined to have been caused in response to a change of state of position detector 22.

As mentioned above, it is envisioned that the remote receiver 34 could conveniently be integrated into a beeper or personal pager system. Circumstances and situations are also easily envisioned where the wireless transmissions of signals called for in this apparatus might be safely and efficiently carried out through one or more dedicated hard lines or through existing house wiring, as an alternative to airborne radio frequency or infrared transmission.

As noted above, the state-changing element of the position-sensitive transducer 40 can be selected from various conventional designs, for instance a gravity switch that closes when the infant moves into a prone position thereby actuating the alarm sequence, or a force or pressure switch operated similarly. The transducer could also be calibrated to produce a continuous signal of varying characteristics reflecting the infant's position, as opposed to the essentially binary position signals discussed above. In addition to control of active transmitter devices, as above, the transducer could be employed to change a remotely-detectable characteristic, for example, to alter the impedance of a coil. The particular selection is one of engineering judgment, guided at least in part by the inherent desirability of minimizing the bulky imposition on the infant. Further, transducer 22 can be attached to the child's clothing as shown in FIG. 1 or alternatively attached directly to the child, held in place by a patch, adhesive, elastic banding or the like. Similarly, transducer 22 can be affixed to virtually any portion of the child's torso, front or back, and arranged to equivalently sense a SIDS-sensitive situation, the decision again being one of engineering judgment based on the transmission capabilities of the selected transducer and the comfort of the infant. Similarly the alarm 60 can provide any of various audible, visual or tactile alarms, or combinations thereof.

In a further alternative embodiment that is presently preferred, the position taken by the sleeping infant is sensed by commercially available sensing devices adapted to respond to the position of a corresponding predetermined marker, such as a coil, a metal disk, a magnet, or a patch of optically contrasting material, affixed to the child or its clothing. In the presently preferred embodiment, the infant's location is illuminated at a low level by an infrared source, and the infant is dressed in a garment having areas of significantly differing reflectivity to infrared radiation. The position of the infant is then determined by an infrared sensor provided so as to "view" the infant's location, e.g., by being suspended over the crib. The optical sensor is calibrated to determine, for example, whether a patch of highly reflective light-colored fabric on the front of the infant's garment, the remainder of the garment being of a dark absorptive material, is exposed to the sensor, enabling ready detection. Change in signal strength received by the sensor responsive to change in the position of the infant is employed to provide an indication of the position assumed by the infant. Sensing of a SIDS-dangerous prone or side-lying position by the sensor activates an alarm, alerting a care-giver of the need to attend to the infant.

Figure 3:
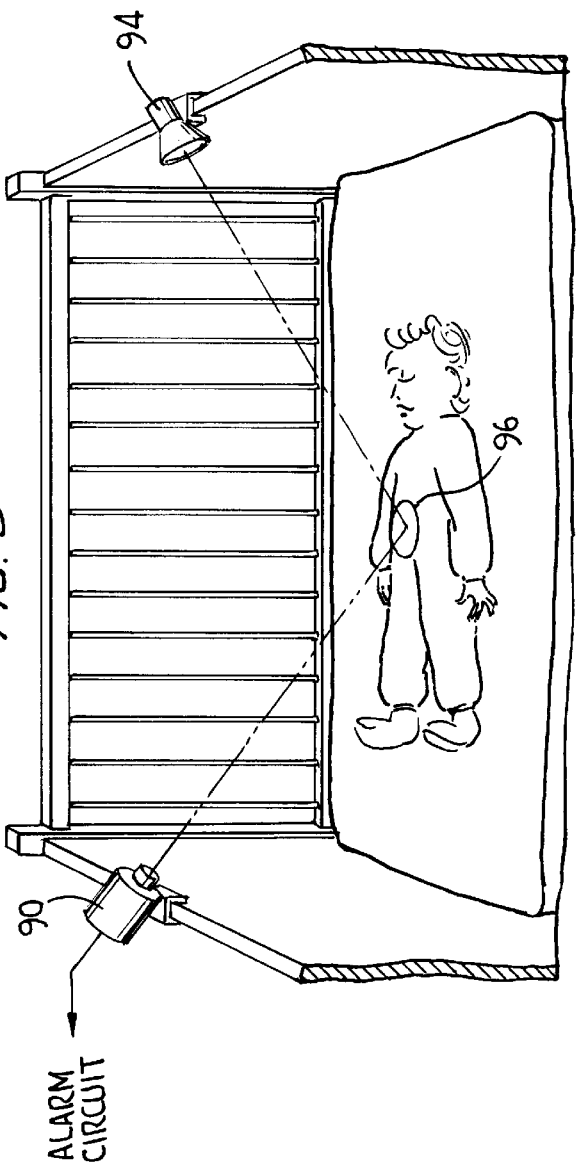
FIG. 3 is a schematic illustration of a further embodiment of the present invention.

An example of such an arrangement employing optical sensing is shown in FIG. 3. Remote sensor 90, trained on the crib with a field of vision sufficiently wide to include the infant's normal range of motion, comprises a video scanner or camera or optical detector focused on a bright, perhaps luminescent, patch or marker 96 attached to the infant's torso or clothing, opposite a source 94 of radiation of wavelength to which the sensor is sensitive; the preferred wavelength may include visible or infrared radiation. Sensor 90 and source 94 may be provided in the same physical package, but are shown separately for clarity. Clearly, the material of the marker must correspond to the wavelength of the radiation emitted by the source; for example, if the source and sensor operate in the infrared, the marker may conveniently be provided as a patch of light-colored, infrared-reflective material on the front of a garment, with the remainder of the garment made of an infrared-absorptive material. The sensitivity of the sensor can be adjusted by the user when putting the infant down, or may be set automatically.

Preferably the marker is a reflective area on the infant's front, as shown, such that the disappearance of the marker from the frame of the sensor would indicate that the infant had rolled over into a side-lying or prone position, and the alarm mechanism (indicated generally at 98) would be initiated as described above to transmit this information via signal 32 to a remote receiver and alarm device 34. One advantage of this arrangement is that failure of the source would activate the alarm. Alternatively and equivalently, the marker could instead be adhered to the infant's back and its detection would signify danger.

Further improvements considered to be within the scope of the invention may include a "System OK" light or other visual or audible indicator 80 included in the remote receiver 34 and activated by a continuously generated signal from the transducer 22 to provide assurance to the care-giver that the system is properly powered and operational. Further, the system can be provided with a time-delay or counter-type filter to prevent system false alarm generation resulting from transient repositioning normal to a baby's sleeping habits.

As mentioned above, a networked system of position sensors according to the invention may be adapted for use in a hospital, nursery or other such facility and multiplexed to provide continuous monitoring of each of a number of infants at a central monitoring station.

Numerous additional modifications and improvements to the embodiments of the invention described will occur to those of skill in the art, and are considered to be equivalents thereof and within the scope of the invention where not specifically excluded by the following claims. The invention is therefore not to be limited by the above exemplary disclosure, but only by the following claims.

What is claimed is:

1. Apparatus for reducing the possibility of sudden infant death syndrome in infants by alerting a care-giver that an infant has moved out of the safe supine position, comprising:
   a. a source of radiation directed generally onto said infant;
   b. a reflector configured as a portion of or affixed to a garment worn by said infant, other portions of said garment having different reflective characteristics with respect to said radiation;
   c. a radiation-sensitive sensor for providing a first signal varying responsive to changes in the amount of said radiation incident thereon;
   d. means responsive to said first signal for producing and transmitting a second signal responsive to the sensed position of the infant;
   e. a remote receiver responsive to said second signal for producing an alarm alerting a care-giver if said infant assumes a predetermined position.

2. The apparatus of claim 1, wherein said radiation is in the infrared.

3. The apparatus of claim 1, wherein said means responsive to said first signal transmits a radio-frequency second signal to said means for producing an alarm.

4. The apparatus of claim 1, wherein said means responsive to said first signal transmits an infrared second signal to said means for producing an alarm.

5. The apparatus of claim 1, wherein said means responsive to said first signal transmits said second signal by wired connection to said means for producing an alarm.

6. The apparatus of claim 1, wherein said receiver for producing an alarm is responsive to a plurality of second signals responsive to the positions of a plurality of infants, and comprises means for differentiating between signals received therefrom.

7. The apparatus of claim 6, wherein said receiver for producing an alarm responsive to a plurality of means for producing second signals comprises means for providing an alarm indicating which of said plurality of infants has assumed a particular position.

8. The apparatus of claim 7, wherein said receiver for producing an alarm responsive to a plurality of said means for producing second signals further comprises means for alerting a care-giver that one of said plurality of infants has assumed a particular position.

9. The apparatus of claim 1, wherein said alarm comprises an audible signal.

10. The apparatus of claim 1, wherein said alarm comprises an visible signal.

11. The apparatus of claim 1, wherein said alarm comprises a tactile signal.

12. The apparatus of claim 1, wherein said second signal is compatible with a paging system.

13. The apparatus of claim 1 further comprising an alarm to awaken the infant upon the sensing of its having assumed the prone position.

14. Method for reducing the possibility of sudden infant death syndrome in an infant by alerting a care-giver that the infant has assumed a potentially dangerous position, comprising the steps of:
   a. directing a source of radiation of predetermined wavelength onto said infant;
   b. affixing a member reflecting said radiation of predetermined wavelength to the infant, such that amount of said radiation reflected by said member varies with the position of the infant;
   c. providing a detector to receive said radiation of predetermined wavelength reflected from said member and produce a first signal proportional to the strength of the reflected radiation thereby indicating the position of said infant;

d. transmitting a second signal responsive to said first signal to a remote receiver; and e. producing an alarm in response to receipt of a second signal indicating the possibility that the infant has assumed a potentially dangerous position.

15. The method of claim 14, wherein said member is removably attached to the clothing of the infant.

16. The method of claim 14, wherein said member is configured as a portion of a garment, other portions of said garment having different reflective characteristics with respect to said radiation of said wavelength.

17. A garment to be worn by an infant while sleeping, and for use in combination with a source of radiation of predetermined wavelength and a detector thereof, said detector being adapted to activate means for providing an alarm signal to a remote caregiver when the detected intensity of radiation from said source falls below a predetermined level, said garment having a portion made of material relatively reflective of radiation of said predetermined wavelength, the remainder of said garment being made of a material relatively absorptive of said radiation of said predetermined wavelength.

* * * * *